US010588718B2

(12) United States Patent
Koo et al.

(10) Patent No.: US 10,588,718 B2
(45) Date of Patent: Mar. 17, 2020

(54) ORTHODONTIC BRACKET

(71) Applicant: BIOCETEC CO., LTD, Seoul (KR)

(72) Inventors: Hong Sik Koo, Seoul (KR); Sung Hee Yoon, Seoul (KR)

(73) Assignee: BIOCETEC CO., LTD, Seoul (KR)

(*) Notice: Subject to any disclaimer, the term of this patent is extended or adjusted under 35 U.S.C. 154(b) by 0 days.

(21) Appl. No.: 15/565,903

(22) PCT Filed: Jul. 28, 2015

(86) PCT No.: PCT/KR2015/007854
§ 371 (c)(1),
(2) Date: Oct. 12, 2017

(87) PCT Pub. No.: WO2016/167414
PCT Pub. Date: Oct. 20, 2016

(65) Prior Publication Data
US 2018/0092716 A1   Apr. 5, 2018

(30) Foreign Application Priority Data
Apr. 15, 2015 (KR) .................. 10-2015-0053458

(51) Int. Cl.
*A61C 7/14* (2006.01)
*A61C 7/28* (2006.01)
*A61C 7/30* (2006.01)

(52) U.S. Cl.
CPC .................. *A61C 7/14* (2013.01); *A61C 7/28* (2013.01); *A61C 7/285* (2013.01); *A61C 7/287* (2013.01); *A61C 7/30* (2013.01)

(58) Field of Classification Search
CPC .. A61C 7/14; A61C 7/12; A61C 7/125; A61C 7/285; A61C 7/287; A61C 7/30; A61C 7/28–287
See application file for complete search history.

(56) References Cited

U.S. PATENT DOCUMENTS

| 4,149,314 A * | 4/1979 | Nonnenmann | A61C 7/285 |
| | | | 433/13 |
| 5,269,681 A * | 12/1993 | Degnan | A61C 7/143 |
| | | | 433/11 |
| 5,322,435 A * | 6/1994 | Pletcher | A61C 7/145 |
| | | | 433/10 |

(Continued)

FOREIGN PATENT DOCUMENTS

| CN | 1494402 A | 5/2004 | |
| EP | 3034030 A1 * | 6/2016 | ............... A61C 7/12 |

(Continued)

OTHER PUBLICATIONS

International Search Report in International Application No. PCT/KR2015/007854, dated Jan. 15, 2016.

*Primary Examiner* — Sean M Michalski
*Assistant Examiner* — Shannel N Wright
(74) *Attorney, Agent, or Firm* — Park, Kim & Suh, LLC

(57) ABSTRACT

Disclosed is an orthodontic bracket. An orthodontic bracket according to an aspect of the present invention comprises a body attached to teeth, a cover linear-movably and rotatably coupled to the body, and an elastic member which applies pressure to the cover so as to keep the cover locked, wherein the cover is locked to the body while pressing a wire such that the wire is seated in the body.

13 Claims, 18 Drawing Sheets

(56) References Cited

U.S. PATENT DOCUMENTS

| | | | | |
|---|---|---|---|---|
| 6,193,508 B1 * | 2/2001 | Georgakis | | A61C 7/287 433/11 |
| 2005/0239012 A1 * | 10/2005 | Bathen | | A61C 7/287 433/10 |
| 2005/0244774 A1 * | 11/2005 | Abels | | A61C 7/285 433/10 |
| 2007/0224569 A1 * | 9/2007 | Oda | | A61C 7/285 433/10 |
| 2007/0243497 A1 * | 10/2007 | Voudouris | | A61C 7/141 433/10 |
| 2008/0057459 A1 * | 3/2008 | Abels | | A61C 7/125 433/10 |
| 2008/0113311 A1 * | 5/2008 | Forster | | A61C 7/287 433/11 |
| 2008/0241782 A1 * | 10/2008 | Abels | | A61C 7/285 433/10 |
| 2010/0159411 A1 | 6/2010 | Oda | | |
| 2011/0183280 A1 * | 7/2011 | Cosse | | A61C 7/14 433/13 |
| 2012/0064476 A1 * | 3/2012 | Sabilla | | A61C 7/285 433/11 |
| 2013/0052604 A1 * | 2/2013 | Hiro | | A61C 7/14 433/9 |
| 2015/0182307 A1 * | 7/2015 | Yick | | A61C 7/125 433/9 |
| 2015/0351873 A1 * | 12/2015 | Sabilla | | A61C 7/285 433/10 |

FOREIGN PATENT DOCUMENTS

| | | | | |
|---|---|---|---|---|
| JP | 2007-252926 A | | 10/2007 | |
| JP | 2015-042297 A | | 3/2015 | |
| KR | 10-0320027 B1 | | 1/2002 | |
| KR | 10-0675673 B1 | | 1/2007 | |
| KR | 10-2007-0070169 A | | 7/2007 | |
| WO | WO 0033760 A1 * | | 6/2000 | A61C 7/28 |

* cited by examiner

ORTHODONTIC BRACKET

CROSS-REFERENCE TO RELATED APPLICATIONS

This application is the National Stage filing under 35 U.S.C. 371 of International Application No. PCT/KR2015/007854, filed on Jul. 28, 2015, which claims the benefit of Korean Patent Application No. 10-2015-0053458, filed on Apr. 15, 2015, the contents of which are all hereby incorporated by reference herein in their entirety.

BACKGROUND

Technical Field

The present invention relates to an orthodontic bracket, more particularly to an orthodontic bracket having a cover.

Description of the Related Art

Malalignment of the teeth or malocclusion (misalignment between the maxillary arch and mandibular arch) may be caused by, among other things, abnormal development of the teeth themselves, bad habits during infancy and childhood such as sucking on the thumb, etc., and bad eating habits. Since malalignment or malocclusion may cause much discomfort in everyday life and may lower self-esteem in the context of social relationships, various orthodontic devices are being used to treat dental malalignment or malocclusion. One such orthodontic device is the bracket, which is adhered and affixed to a tooth and connected with a wire.

From among the types of orthodontic brackets, the self-ligating bracket is a type that does not require a ligation operation. Since the self-ligating bracket does not entail the inconvenience of mounting a ligature to the orthodontic bracket, the time required for the procedure can be reduced, and since there is no food residue retained on the ligature or on the orthodontic bracket because of an installed ligature, the oral cavity can be kept in a more hygienic state.

SUMMARY OF THE INVENTION

Technical Problem

To address the issues described above, an aspect of the present invention aims to provide an orthodontic bracket that is convenient to use.

Other objectives of the present invention will be more clearly understood from the embodiments of the invention set forth below.

Technical Solution

An orthodontic bracket according to an aspect of the invention may include: a body configured to be adhered to a tooth; a cover coupled to the body such that the cover is capable of linear and rotational movement; and an elastic member configured to press the cover to maintain a locked state of the cover, where the cover may be locked onto the body while pushing on a wire to keep the wire in place in the body.

An orthodontic bracket according to an aspect of the invention according to an embodiment of the invention can include one or more of the following features. For example, the body can include a body locking part on which the cover may be latched, a guide part that guides the cover, and a wire insertion part into which the wire may be inserted, while the cover can include a cover locking part that may be latched onto the body locking part and a hinge part that may be coupled to the guide part.

The body locking part can include a locking protrusion and a cover holder recess, the cover holder recess formed on the inside of the locking protrusion and configured to receive a portion of the cover inserted therein; the guide part can include a guide recess; the hinge part can be inserted into the guide recess in a manner that enables linear and rotational movement; and the cover locking part can be inserted into the cover holder recess and latched onto the locking protrusion.

The locking protrusion can include a latching protrusion, and the cover locking part can include a latching recess into which the latching protrusion may be inserted.

In the cover holder recess, an elastic member insertion recess can be formed, into which the elastic member may be inserted.

The hinge part can include a rotation recess configured to hold the guide part and enable the cover to rotate.

The body locking part can include a locking protrusion slope, and the cover can move downward along the locking protrusion slope when the cover is coupled with the body.

The guide recess can be formed in a sloping fashion. Also, a guide recess can be formed in each of the left and right sides of the guide part.

An auxiliary elastic member can additionally be included, which may be configured to elastically press the cover, and the guide part can have an auxiliary elastic member insertion recess formed, into which the auxiliary elastic member may be inserted.

The cover can include a cover top surface and a cover sloped surface, and when the cover is coupled to the body, the cover sloped surface can contact the body locking part to stop the progress of the cover.

In any one of the cover top surface and the cover sloped surface, a cover recess can be formed in intaglio.

The guide part can have a smaller width than the body and can be arranged at the center of the body, whereas the cover can have the same width as the body.

The hinge part can cover the entire guide recess. Also, the cover locking part can cover a side surface of the body locking part.

Advantageous Effects

An embodiment of the present invention can provide an orthodontic bracket that is convenient to use.

DETAILED DESCRIPTION OF THE INVENTION

Figure 1:
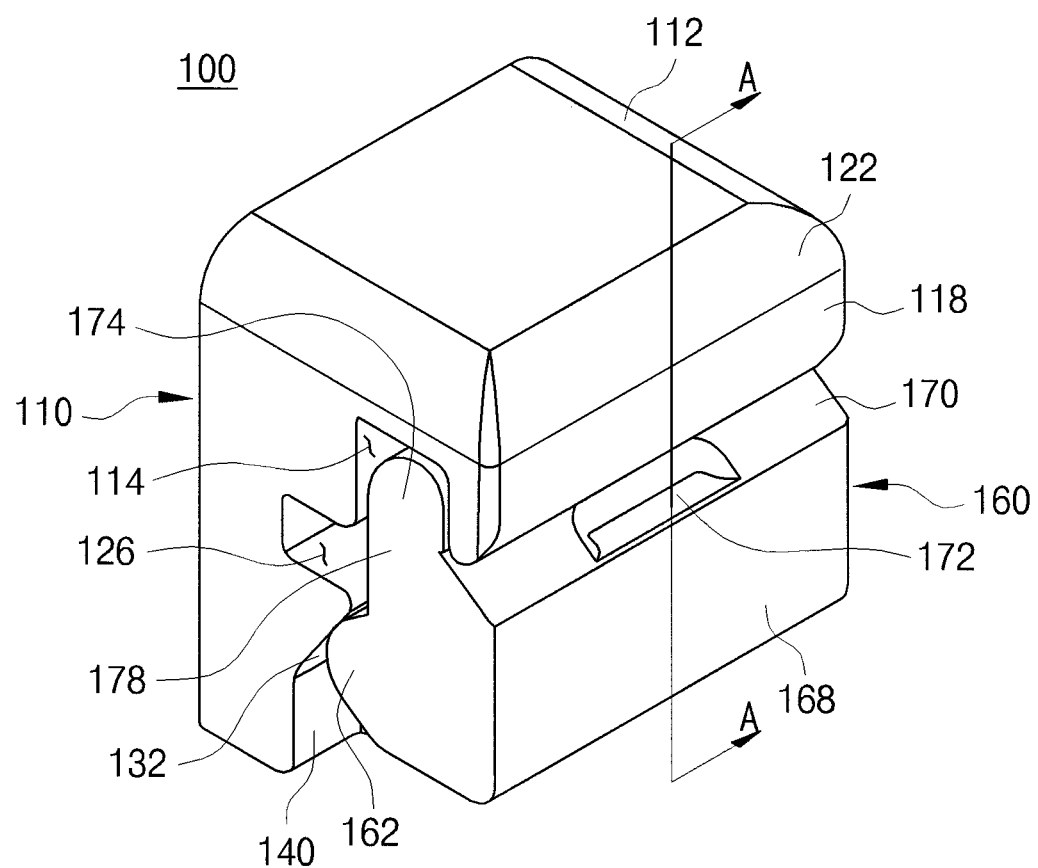
FIG. 1 and FIG. 2 are perspective views illustrating an orthodontic bracket in a locked state according to an embodiment of the invention.

As the invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In the description of the present invention, certain detailed explanations of the related art are omitted when it is deemed that they may unnecessarily obscure the essence of the present invention.

The terms used in the present specification are merely used to describe particular embodiments, and are not intended to limit the present invention. An expression used in the singular encompasses the expression of the plural, unless it has a clearly different meaning in the context. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Terms such as "first", "second", "upper", "lower", "auxiliary", etc., can be used in describing various elements, but the components are not to be limited by such terms. The terms are used only to differentiate one element from another.

A bracket 100 according to an embodiment of the invention described below can be coupled with a wire W having any of a variety of diameters, where the diameter of the wire can be selected as needed from various options. Also, a wire can be selected for use from wires of a maximum diameter, a minimum diameter, and intermediate diameters in consideration of the size and purpose, etc., of the bracket 100, where the cross section of the wire can have a circular, elliptical, polygonal, or any of a variety of shapes.

Certain embodiments of the present invention are described below in more detail with reference to the accompanying drawings. In the description of the invention with reference to the accompanying drawings, the same or corresponding elements may be rendered the same reference numeral, regardless of the figure number, and redundant descriptions may be omitted.

Figure 2:
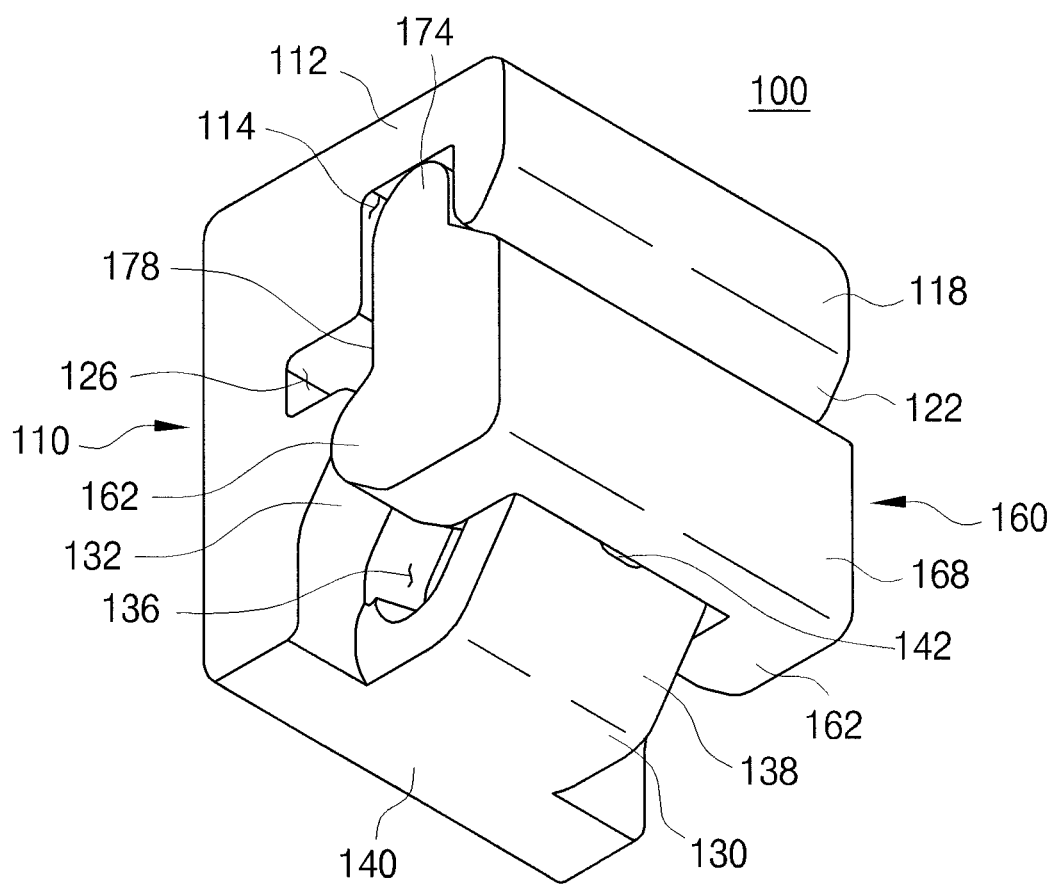
Figure 3:
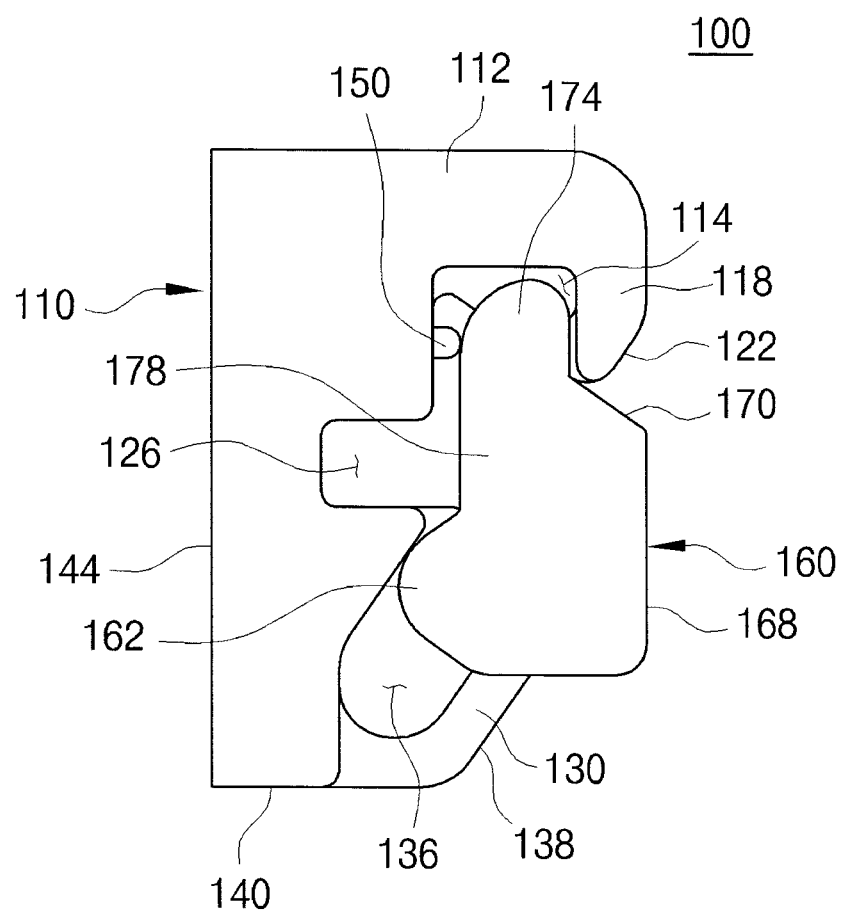
FIG. 3 is a side-elevational view of the orthodontic bracket illustrated in FIG. 1.

FIG. 1 and FIG. 2 are perspective views illustrating an orthodontic bracket 100 in a locked state according to an embodiment of the invention. FIG. 3 is a side-elevational view of the orthodontic bracket 100 illustrated in FIG. 1.

Figure 4:
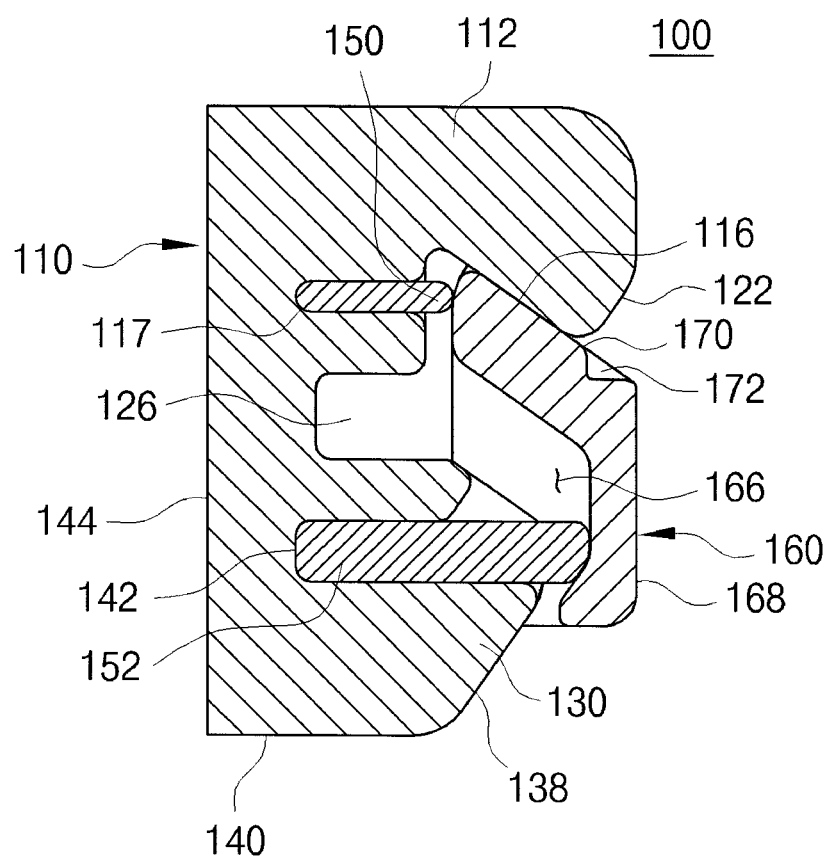
FIG. 4 is a cross-sectional view of the orthodontic bracket across line AA in FIG. 1.

FIG. 4 is a cross-sectional view of the orthodontic bracket 100 across line AA in FIG. 1.

Referring to FIG. 1 through FIG. 4, an orthodontic bracket 100 according to an embodiment of the invention may be a self-ligating bracket and may include a body 110 that is secured to a tooth, a cover 160 that is coupled in a manner that allows linear and rotational movement with respect to the body 110, and an elastic member 150 and an auxiliary elastic member 152 that press the cover 160 upwards from an inner side of the cover 160. Since the cover 160 pushes a wire (not shown) by way of rotation to keep the wire in place within the wire insertion part 126 of the body 110, the orthodontic bracket 100 according to this embodiment allows convenient use, even in the case of irregular teeth alignment, as the cover 160 can close and push on the wire.

The cover 160 may have the same width as the body 110, in effect completely covering the upper portion of the wire (not shown) and preventing foreign substances from entering between the body 110 and the cover 160. Also, since the cover 160 is pressed upwardly by the elastic member 150 and auxiliary elastic member 152, when in a coupled state with the body 110, the cover 160 can be kept locked in a stable manner, and the cover 160 can be prevented from becoming detached from the body 110.

The body 110 and the cover 160 can be formed from the same material and by the same manufacturing method, such as by plastic injection molding or ceramic sintering, for example. The elastic member 150 and the auxiliary elastic member 152 can be fabricated using an elastic material (for instance, metal or plastic, etc.).

Below, a description is provided of the body 110 of an orthodontic bracket 100 according to this embodiment, with reference to FIG. 5 through FIG. 8.

Figure 5:
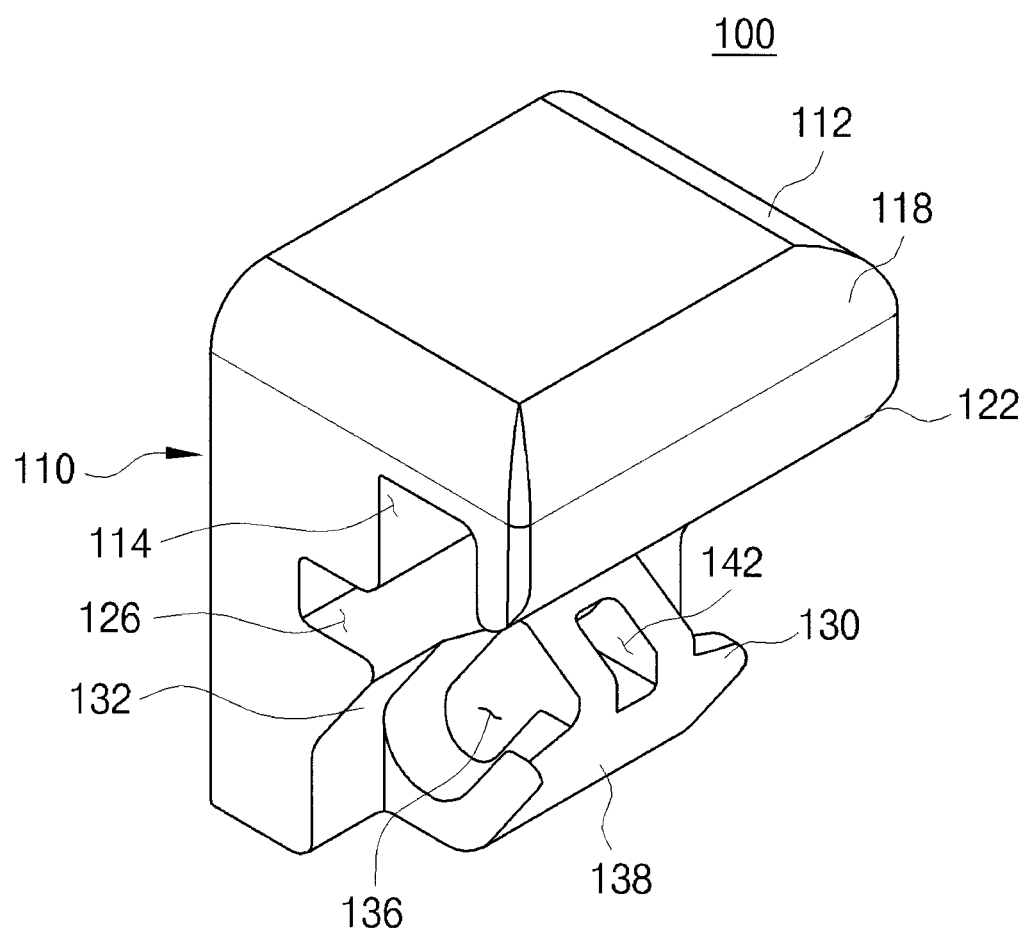
FIG. 5 through FIG. 7 are perspective views illustrating the body of the orthodontic bracket illustrated in FIG. 1.
Figure 6:
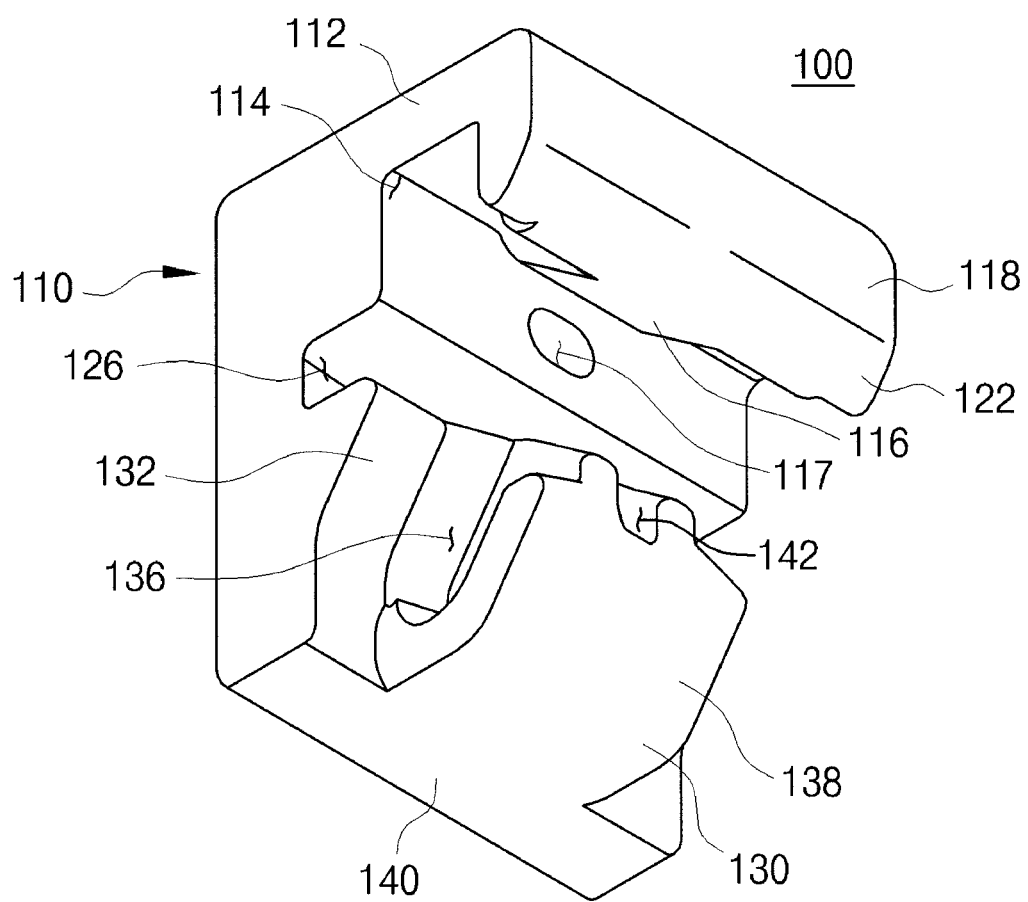
Figure 7:
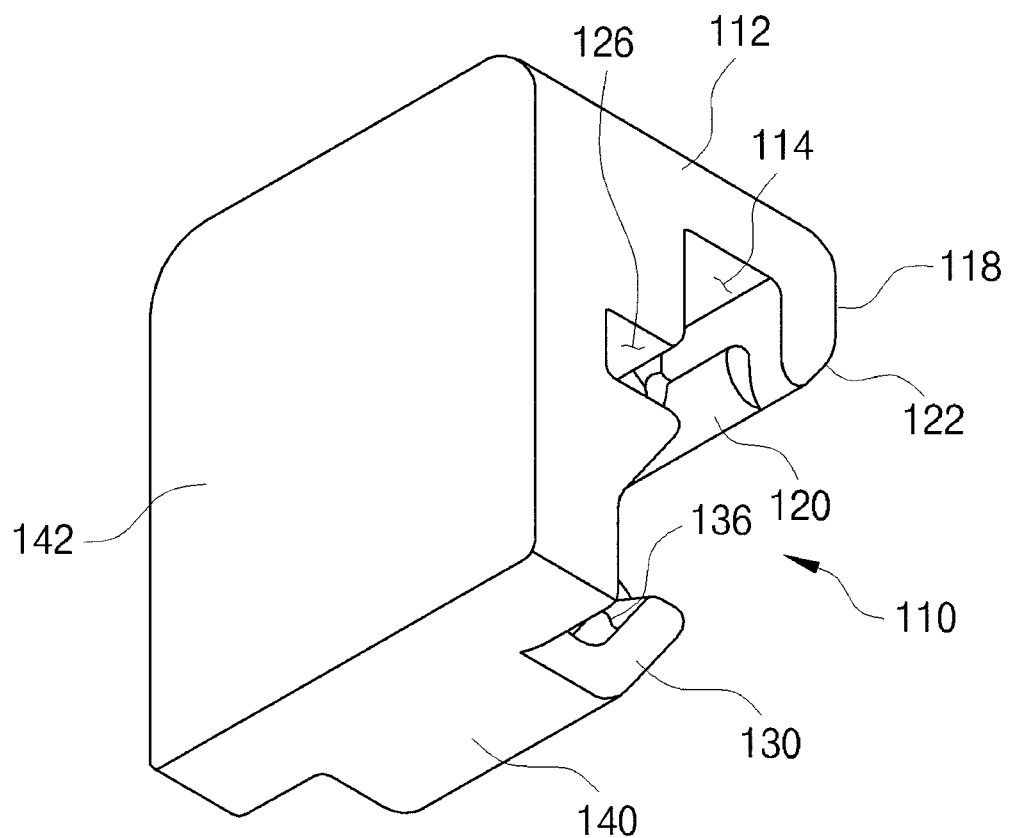
Figure 8:
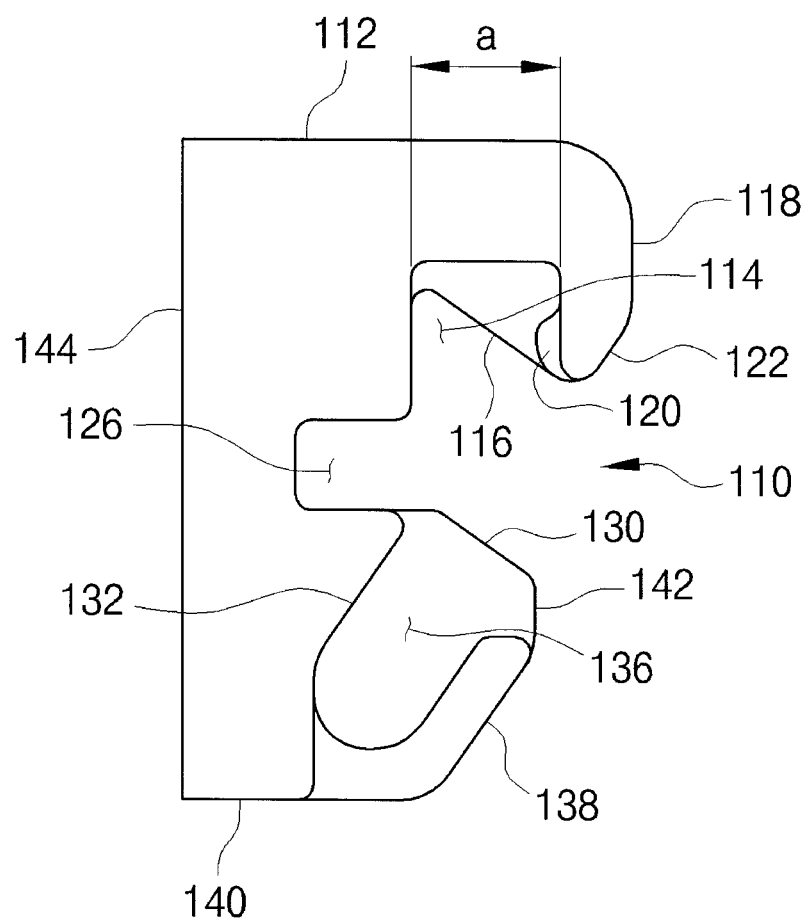
FIG. 8 is a side-elevational view of the body illustrated in FIG. 5.

FIG. 5 through FIG. 7 are perspective views illustrating the body of the orthodontic bracket illustrated in FIG. 1, and FIG. 8 is a side-elevational view of the body illustrated in FIG. 5.

Referring to FIG. 5 through FIG. 8, the body 110 may be adhered to a tooth (not shown) and may be coupled with the cover 160 to secure the wire (not shown). The body 110 may include a body locking part 112, a wire insertion part 126, and a guide part 130.

The body locking part 112, for maintaining the locked state between the body 110 and the cover 160, may include a cover holder recess 114 and a locking protrusion 118.

The locking protrusion 118 may protrude in an L shape from an upper end of the body 110. On the inner side of the locking protrusion 118, a pair of latching protrusions 120 may be formed. When the cover 160 is coupled to the body 110, the latching protrusions 120 may be inserted into the latching recesses 176 of the cover 160. At the center of a latching protrusion, a sloping protrusion 116 may be formed.

A locking protrusion slope 122 may be formed at a front end of the locking protrusion 118. The locking protrusion slope 122 may have a particular angle of inclination, so that when the cover 160 is coupled to the body 110, the cover 160 can slide over the locking protrusion slope 122 and enter the guide part 130 of the body 110 in a stable manner (see FIG. 13). The inclination angle of the locking protrusion slope 122 can be formed the same as or almost the same as the inclination angle of a guide recess 136 of the guide part 130. Also, when the cover 160 is removed from the body 110, the locking protrusion slope 122 may allow a tool (not shown) to be readily inserted into the cover recess 172 formed in the cover 160 (see FIG. 1).

The cover holder recess 114, which is a recess formed by the locking protrusion 118, corresponds to the portion into which the cover locking parts 174 of the cover 160 may be inserted. The cover holder recess 114 may be formed along the entire width of the body 110 and may have a substantially quadrilateral shape. The width (see reference numeral a of FIG. 8) of the cover holder recess 114 may be formed somewhat larger than the thickness of the cover locking parts 174 of the cover 160. Because of this, the cover locking parts 174 inserted into the cover holder recess 114 can be made capable of a certain degree of upward movement when an elastic force is applied by the elastic member 150 or auxiliary elastic member 152.

The sloping protrusion 116 may be formed on the inner side of the cover holder recess 114. The sloping protrusion 116, which is a sloping surface located at the center on the inner side of the locking protrusion 118, may not only reinforce the strength of the locking protrusion 118 but may also be inserted between the cover locking parts 174 of the cover 160, when the cover 160 is coupled to the body 110, to prevent the cover 160 from becoming separated.

In one side of the cover holder recess 114, an elastic member insertion recess 117 may be formed. The elastic member 150 may be inserted into the elastic member insertion recess 117 with a portion protruding outwards.

The wire insertion part 126, which is a recess formed in the center of the body locking part 112 and guide part 130, may be formed along the entire width of the body 110. While an example is presented in which the cross section of the wire insertion part 126 has a quadrilateral shape, various other shapes, such as circular and elliptical shapes among others, can obviously be used. The wire insertion part 126 can be formed greater than the maximum diameter of a wire that can be used for the bracket 100, so that the wire can be inserted into the wire insertion part 126.

The guide part 130 may couple with the cover 160 to provide guidance enabling the linear and rotational movement of the cover 160. The guide part 130 can be formed in a sloped configuration with respect to the adhesion surface 144 of the body 110, allowing the cover 160 to be readily coupled to the guide part 130, which is located lower than the locking protrusion 118. Of course, the guide part 130 can also be formed parallel to the adhesion surface 144.

The width of the guide part 130 may be formed smaller than that of the body 110. Because of this, when the cover 160 is coupled to the guide part 130, the guide part 130 may be located between the cover locking parts 174 of the cover 160 (see FIG. 2).

The guide part 130 may protrude upward from a guide lower slope surface 132 and may include a pair of guide recesses 136, a guide upper slope surface 138, and an auxiliary elastic member insertion recess 142.

The guide recesses 136 may be recesses formed with an inclination angle at the left and right sides of the guide part 130 and can have one end (entrance) open to allow the cover locking parts 174 of the cover 160 to be inserted therein and the other end closed to limit the movement of the cover locking parts 174. The cover locking parts 174 may be capable of linear movement or rotational movement while inserted in the guide recesses 136. The guide recesses 136 may be formed symmetrically in both sides, i.e. the left and right sides, of the guide part 130, so that the cover 160 can be supported in a stable manner.

The guide upper slope surface 138 may correspond to the upper surface of the guide part 130 and may have the same angle of inclination as the guide recesses 136. The guide upper slope surface 138 may be connected with the guide lower surface 140, which corresponds to the lower surface of the body 110.

In the center of the upper part of the guide part 130, auxiliary elastic member insertion recess 142 may be formed. The auxiliary elastic member 152 may be inserted into the auxiliary elastic member insertion recess 142 with a portion protruding upwards (see FIG. 4).

The body 110 may include an adhesion surface 144 that is formed in a flat shape and is adhered to a tooth. The adhesion surface 144 can have several protrusions (not shown) formed for increased adhesion and can obviously be formed in various other shapes, such as a curved shape, etc., instead of a planar shape.

Figure 9:
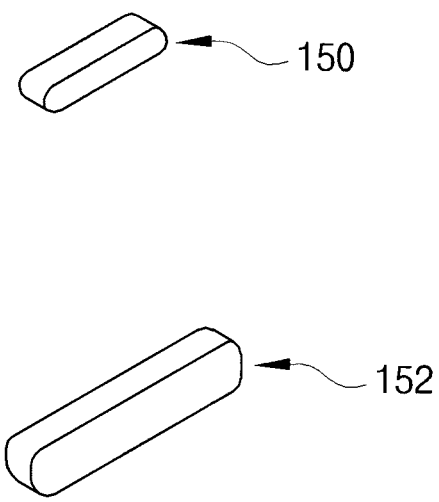
FIG. 9 is a perspective view illustrating an elastic member and an auxiliary elastic member.

FIG. 9 is a perspective view illustrating an elastic member 150 and an auxiliary elastic member 152.

Referring to FIG. 9, the elastic member 150 and the auxiliary elastic member 152 may be shaped as bars of specified lengths, where the auxiliary elastic member 152 can be formed somewhat longer compared to the elastic member 150. When the cover 160 is coupled to the body 110, the elastic member 150 and the auxiliary elastic member 152 may elastically press the cover 160 upward to both maintain a firmly locked state and prevent the cover 160 from becoming detached from the body 110.

The elastic member 150 and the auxiliary elastic member 152 can be fabricated, among other things, from a material having elasticity (e.g. plastic or metal), and can be shaped not only in bar-like shapes but also in various other shapes such as coil springs, etc.

Below, a description is provided of the cover 160 of an orthodontic bracket 100 according to this embodiment, with reference to FIG. 10 through FIG. 12.

Figure 10:
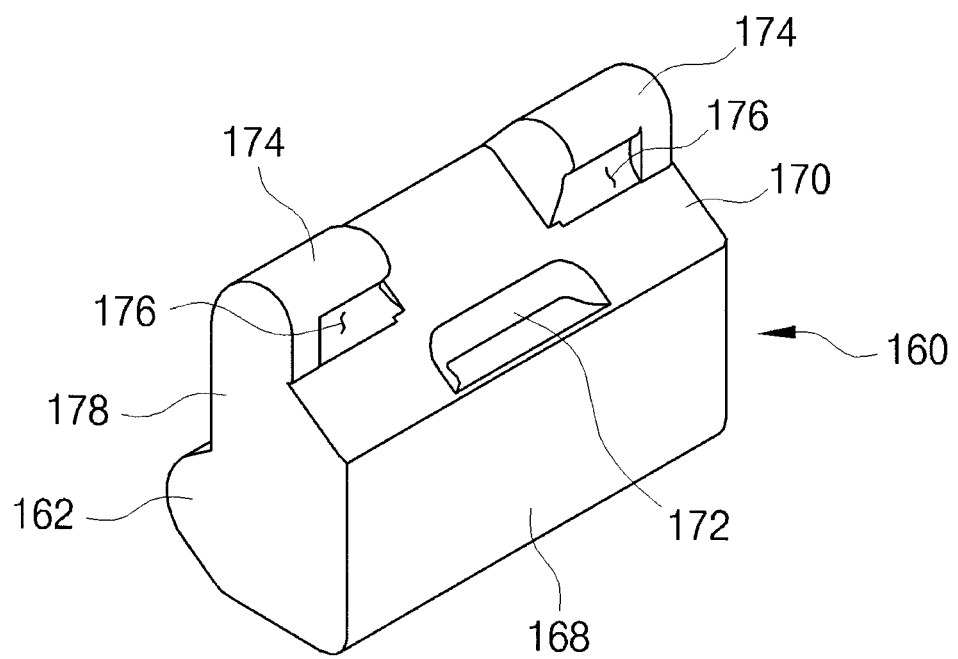
FIG. 10 and FIG. 11 are perspective views illustrating the cover of the orthodontic bracket illustrated in FIG. 1.
Figure 11:
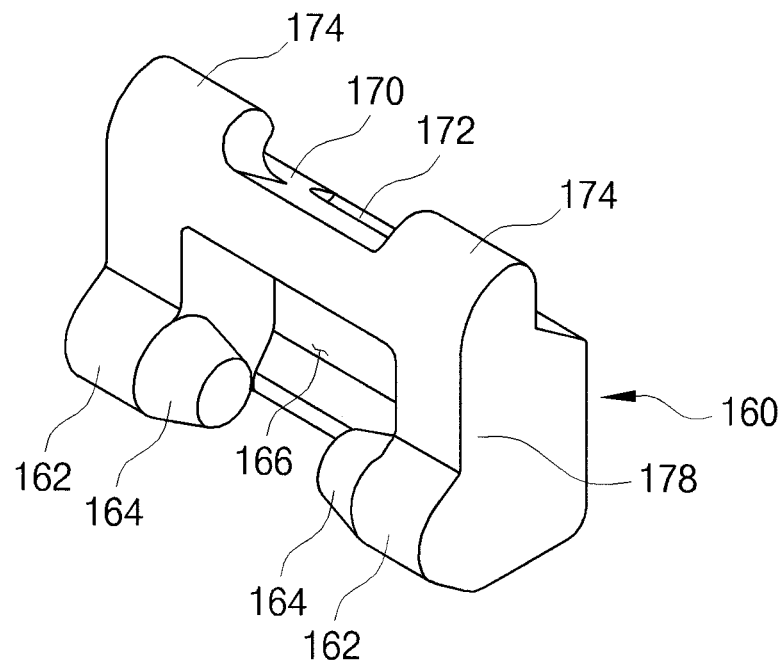
Figure 12:
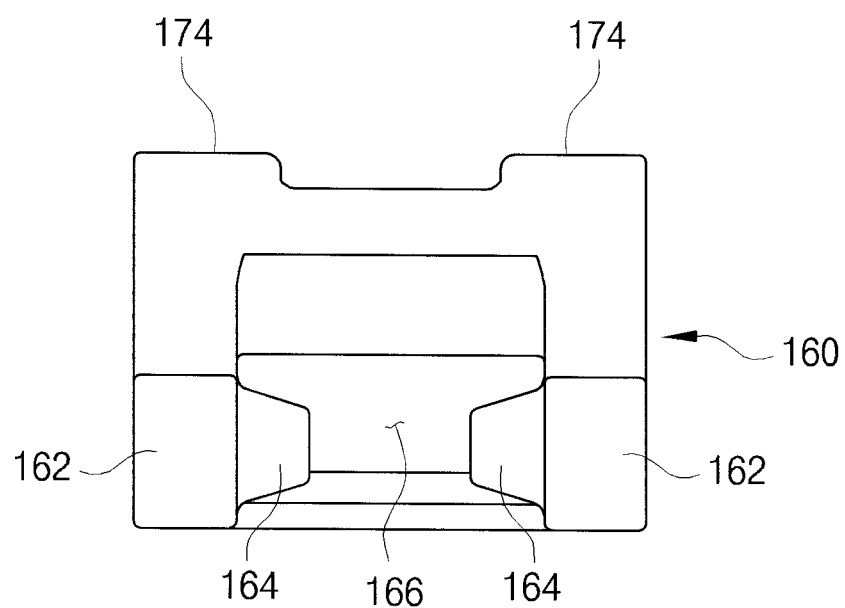
FIG. 12 is a rear-elevational view of the cover illustrated in FIG. 10.

FIG. 10 and FIG. 11 are perspective views illustrating the cover 160 of the orthodontic bracket 100 illustrated in FIG. 1, and FIG. 12 is a rear-elevational view of the cover 160 illustrated in FIG. 10.

Referring to FIG. 10 through FIG. 12, the cover 160 may include a hinge part 162, a cover top surface 168, a cover sloped surface 170, and cover locking parts 174.

The hinge part 162 may be coupled to the guide part 130 in a manner that allows linear and rotational movement and may include a pair of hinge protrusions 164 formed symmetrically. The pair of hinge protrusions 164 may be face each other with a particular interval in-between. Between the hinge protrusions 164, a rotation recess 166 may be formed in intaglio. The hinge protrusions 164 may be inserted into the guide recesses 136 of the guide part 130 to undergo linear movement or rotation movement. The hinge protrusions 164 may have a frustoconical shape, but this is merely given as an example, and the present invention is not to be limited by the shapes of the hinge protrusions 164.

The rotation recess 166, which is a recess formed in intaglio between the hinge protrusions 164, may hold a portion of the guide part 130 to enable a rotation of the cover 160.

The cover top surface 168 and the cover sloped surface 170 may be surfaces that are exposed to the exterior and may be formed continuously with respect to each other. Referring to FIG. 1 through FIG. 4, the cover top surface 168 may be located parallel to the adhesion surface 144 of the body 110, while the cover sloped surface 170 may have an inclination angle in an opposite direction to the locking protrusion slope 122. In the cover sloped surface 170, an intaglio cover recess 172 may be formed. The cover recess 172 may correspond to the recess into which a tool (not shown) such as a set of tweezers may be inserted when the cover 160 is removed from the body 110.

In the cover sloped surface 170, a pair of cover locking parts 174 may be formed. The pair of cover locking parts 174 may be formed in a left-right symmetrical configuration with a particular interval in-between. A cover locking part 174 may have its front end formed in a circular shape and may have a latching recess 176 formed in intaglio in its upper surface.

The cover locking parts 174 may be the portions that are inserted into the cover holder recess 114 of the body locking part 112, and into the latching recesses 176 formed in the upper surfaces, the latching protrusions 120 may be inserted. Because of this, the cover locking parts 174 may not easily become detached from the cover holder recess 114.

Below, a description is provided of the coupling between the body 110 and the cover 160 of an orthodontic bracket 100 according to this embodiment, with reference to FIG. 1 through FIG. 4 as well as FIG. 13.

Figure 13:
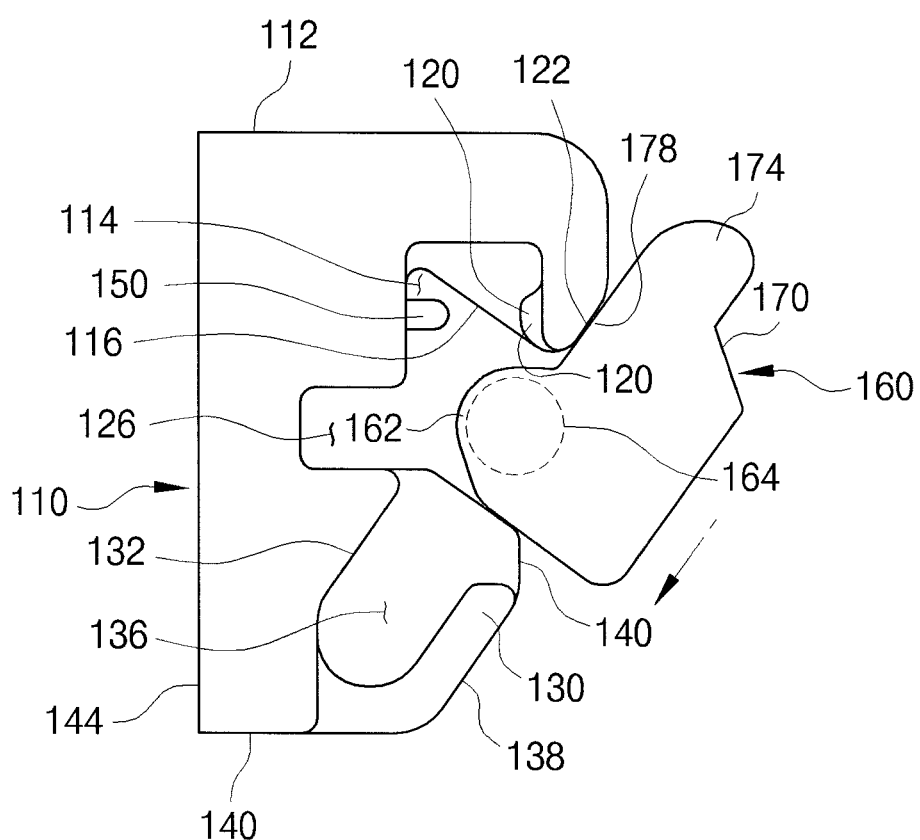
FIG. 13 is a diagram illustrating the cover coupled to the body in an orthodontic bracket according to an embodiment of the invention.

FIG. 13 is a diagram illustrating the cover 160 coupled to the body 110 in an orthodontic bracket 100 according to an embodiment of the invention.

Referring to FIG. 1 through FIG. 4 and FIG. 13, in order to couple the cover 160 with the body 110, the cover top surface 168 of the cover 160 may be arranged parallel to the guide recesses 136 of the body 110, after which the hinge protrusions 164 may be inserted into the guide recesses 136. Here, since the locking protrusion slope 122 of the locking protrusion 118 is formed with an inclination, the side 178 of the cover 160 can slide over the locking protrusion slope 122 to be readily coupled in place. When the hinge protrusions 164 are completely inserted in the guide recesses 136, the cover 160 can rotate and maintain a completely open state (see FIG. 14).

The elastic member 150 and auxiliary elastic member 152 can be inserted in the elastic member insertion recess 117 and auxiliary elastic member insertion recess 142, respectively, before or after the cover 160 is coupled. FIG. 13 provides an example in which the elastic member 150 is inserted before the cover 160 is coupled whereas the auxiliary elastic member (not shown) is inserted afterwards.

Below, a description is provided of the operation of an orthodontic bracket 100 according to this embodiment, with reference to FIG. 14 through FIG. 18.

FIG. 14 through FIG. 18 are diagrams sequentially illustrating a process by which the cover 160 may be locked to the body 110 in an orthodontic bracket 100 according to an embodiment of the invention. Incidentally, FIG. 14 through FIG. 18 are cross-sectional views of the bracket 100, but the hatching for the body 110 and the cover 160 have been omitted.

Figure 14:
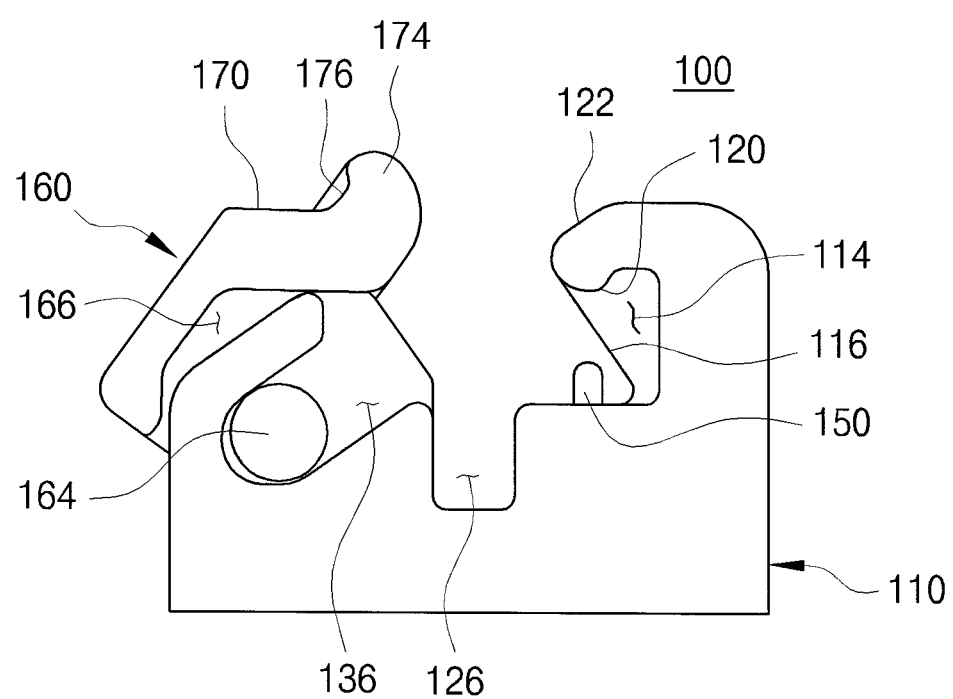
FIG. 14 through FIG. 18 are diagrams sequentially illustrating a process by which the cover may be locked to the body in an orthodontic bracket according to an embodiment of the invention.

Referring to FIG. 14, with the hinge protrusions 164 positioned at the ends opposite the entrances of the guide recesses 136, the cover 160 can be rotated to maintain a completely open state. Here, the elastic member 150 may protrude from the cover holder recess 114, and the auxiliary elastic member 152 (not shown in FIG. 14) may also partially protrude from the guide part 130.

Figure 15:
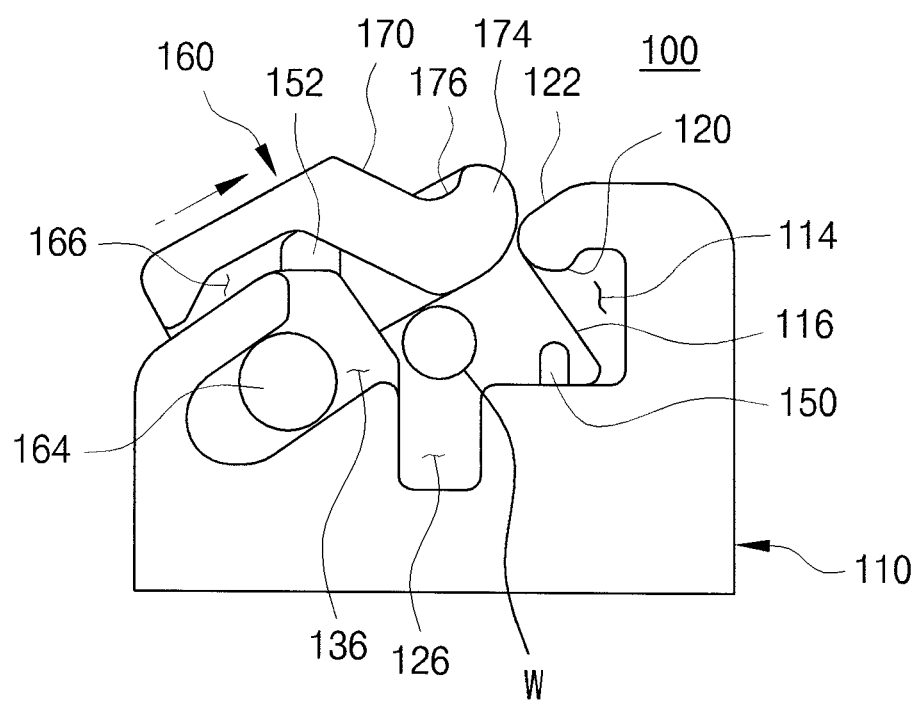
Figure 16:
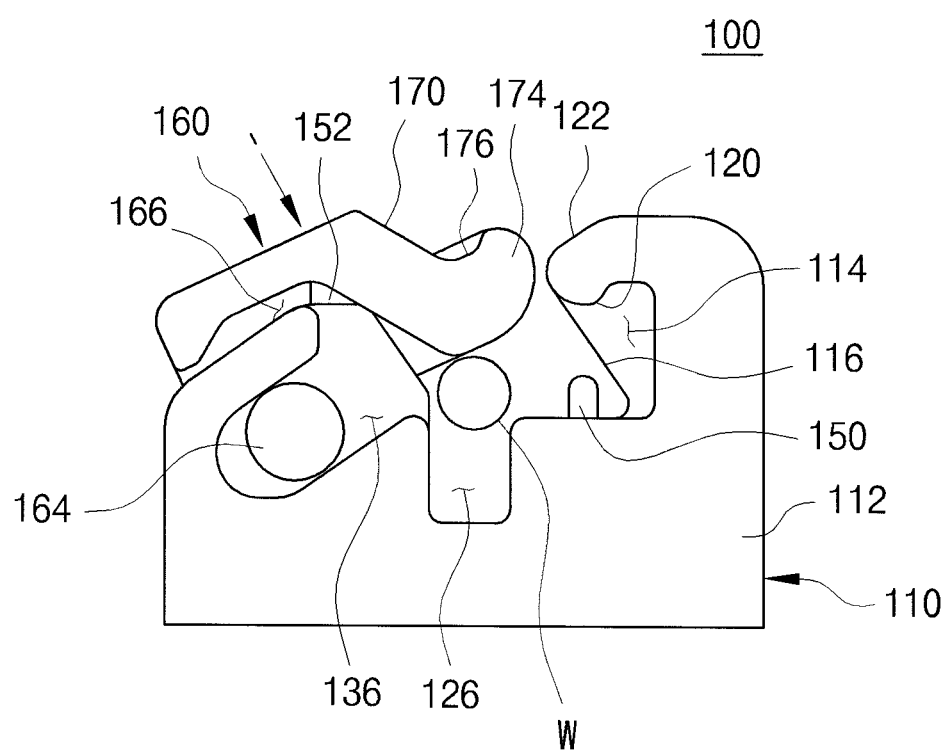

Referring to FIG. 15 and FIG. 16, the cover 160 may be pushed up from the state shown in FIG. 14 following the direction of the arrow marked in FIG. 15, whereby the wire W may be positioned below the cover 160. Although it can be difficult to insert a wire W into the wire insertion part 126 in the case of irregular teeth alignment, pushing the cover 160 along the diagonal direction of the arrow marked in FIG. 16, in a bracket 100 according to the present embodiment, makes it possible to couple the cover 160 with the body 110 while at the same time inserting the wire W into the wire insertion part 126.

Figure 17:
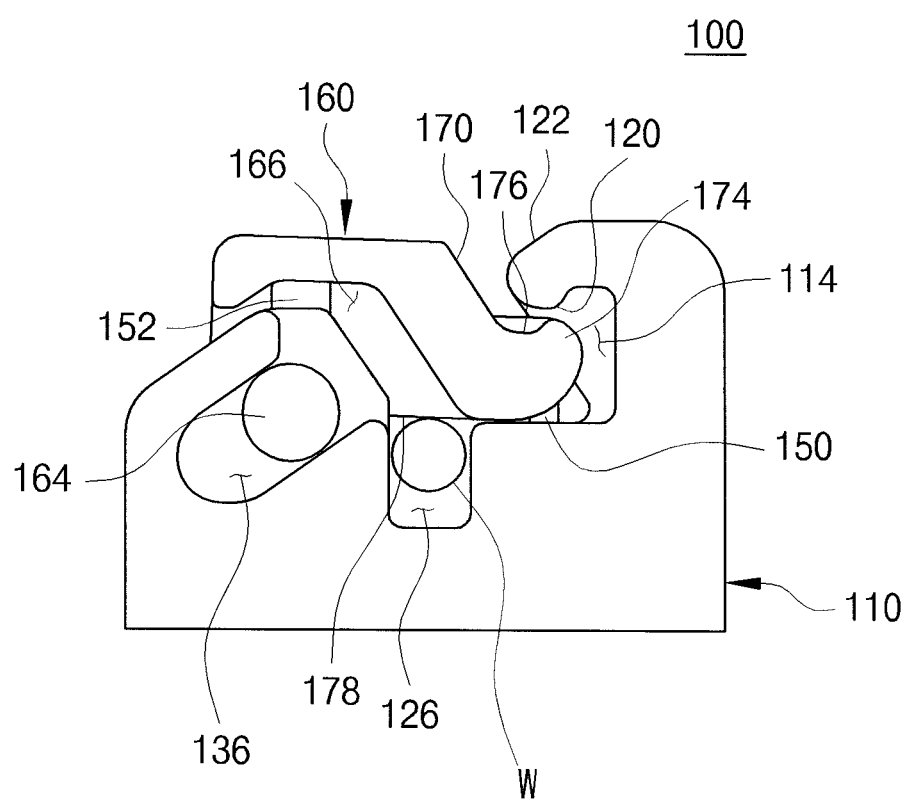

In FIG. 16, when the cover 160 is pressed downward in the direction of the arrow, the cover locking parts 174 may slope and/or rotate downward, with the inner surface of the cover 160 and the guide part 130 of the body 110 in contact with each other, and may move in the direction of the latching protrusions 120 of the body locking part 112, resulting in the configuration shown in FIG. 17.

Referring to FIG. 17, the downwardly pressed cover 160 may have the cover locking parts 174, which correspond to the front end of the cover 160, entering the cover holder recess 114. Here, the elastic member 150, which protrudes while located in the cover holder recess 114, may be pressed and elastically by the cover 160, and likewise the auxiliary elastic member 152 may also be pressed and elastically by the cover 160. Also, the wire W may be downwardly pressed by the cover 160 to be completely inserted in the wire insertion part 126. Referring to FIG. 17, it can be seen that the entrance to the wire insertion part 126 is completely covered by the side 178 of the cover 160.

Figure 18:
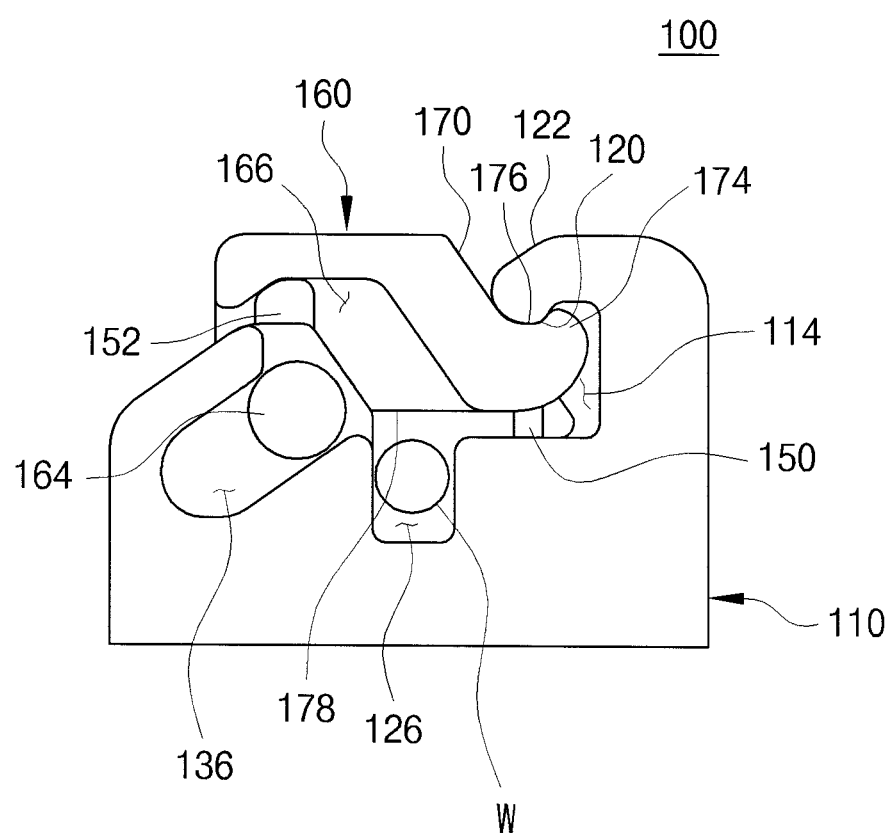

Referring to FIG. 18, if the external force is removed after the cover locking parts 174 of the cover 160 are completely inserted in the cover holder recess 114, the cover 160 may be pressed upwardly due to the elastic recovering forces of the elastic member 150 and auxiliary elastic member 152. Thus, the cover 160 may rise, and the latching protrusions 120 of the locking protrusion 118 may be inserted in the latching recesses 176 of the cover locking parts 174, so that the locked state may be maintained. Also, the sloping protrusion 116 of the cover holder recess 114 may be inserted in the space between the pair of cover locking parts 174 to prevent the cover 160 from becoming separated.

In this way, the elastic member 150 and auxiliary elastic member 152 may elastically press the cover 160 to maintain a locked state and prevent the hinge protrusions 164 of the cover 160 from leaving the guide recesses 136. Although the bracket 100 according to the present embodiment is described above as including an elastic member 150 and an auxiliary elastic member 152, another embodiment of the invention can include the elastic member 150 only without including the auxiliary elastic member 152. Also, the present invention is not to be limited by the positions of the elastic member 150 and auxiliary elastic member 152. For example, a bracket according to another embodiment of the invention can include only the elastic member 150 without including the auxiliary elastic member 152, where the elastic member 150 can be inserted in the auxiliary elastic member insertion recess 142 illustrated in FIG. 4 instead of the cover holder recess 114.

Referring to FIG. 4 and FIG. 18, when the cover 160 is inserted in and completely coupled to the body 110, the elastic forces of the elastic member 150 and auxiliary elastic member 152 may cause the cover 160 to be separated upward by a particular gap from the body 110, while the elastic member 150 and auxiliary elastic member 152 may be elastically deformed by the cover 160.

To release the coupling of the cover 160 and body 110, the procedures illustrated in FIG. 14 through FIG. 18 may be performed in a backward sequence. Here, as there is a cover recess 172 formed in the cover sloped surface 170 of the cover 160, the cover 160 can be readily removed by inserting a set of tweezers, etc., into the cover recess 172 and pushing backwards.

Below, a description is provided of an orthodontic bracket 100 according to another embodiment of the invention, with reference to FIG. 19 and FIG. 20.

Figure 19:
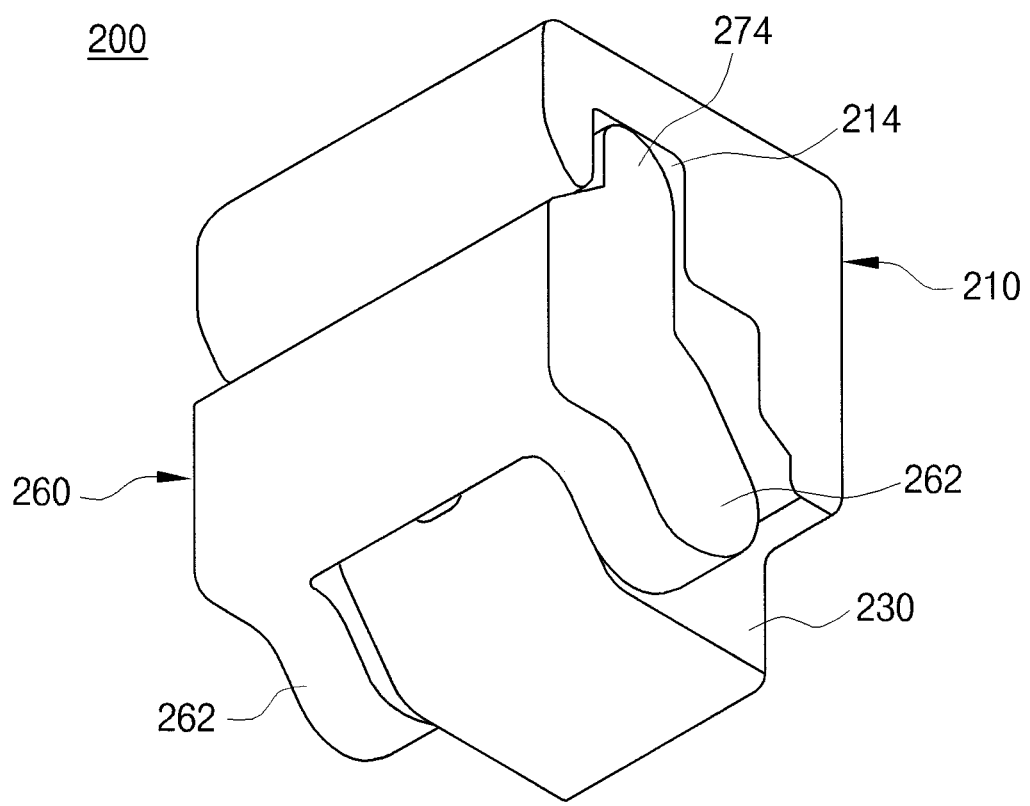
FIG. 19 is a perspective view illustrating an orthodontic bracket according to another embodiment of the invention.
Figure 20:
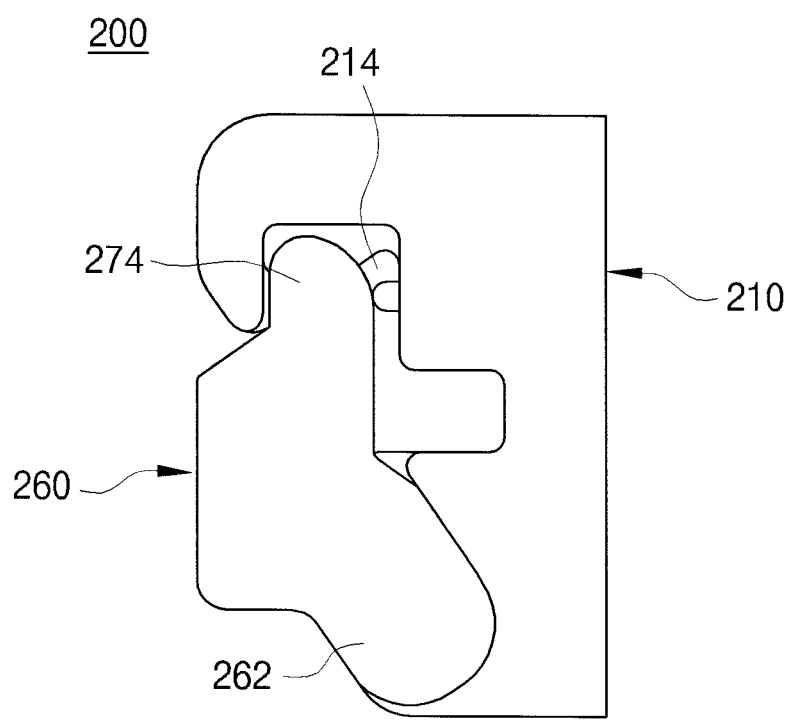
FIG. 20 is a side-elevational view of the orthodontic bracket illustrated in FIG. 19.

FIG. 19 is a perspective view illustrating an orthodontic bracket 200 according to another embodiment of the invention, and FIG. 20 is a side-elevational view of the orthodontic bracket 200 illustrated in FIG. 19.

The elements of an orthodontic bracket 200 according to this embodiment are mostly the same as those of the orthodontic bracket 100 of the previously described embodiment, with the exception that the compositions of the guide part 230 of the body 210 and the hinge part 262 of the cover 260 are different.

The composition of the body 210 may be generally the same as that of the body 110 of the orthodontic bracket 100 according to the previously described embodiment, but the shape of the guide part 230 may be different. The guide part 230 may be formed with a smaller width than the width of the body 210, instead of being the same. In the left and right sides of the guide part 230, guide recesses may be formed, which are not shown in the drawings. The guide recesses may be the same as those of the orthodontic bracket 100 according to the previously described embodiment, and as such, are not described again in detail here.

The cover 260 may include a hinge part 262 that couples to the guide part 230 in a manner that enables movement and rotation, providing substantially the same function as the hinge part 162 of the orthodontic bracket 100 according to the previously described embodiment. However, the hinge part 262 may be formed somewhat longer to completely cover the guide recesses formed in the left and right sides of the guide part 230. The hinge part 262 can completely cover the guide recesses of the guide part 230 both when the cover 260 is locked onto the body 210 and when the lock is released. This can prevent the entry of foreign substances into the guide recesses.

Similarly, the cover locking parts 274 of the cover 260 can also be formed with somewhat thicker sides to prevent the entry of foreign substances into the cover holder recess 214.

While the present invention is described above using certain embodiments of the present invention, the person having ordinary skill in the art would understand that the invention can be modified and altered in various ways without departing from the spirit and scope of the present invention recited in the claims below.

What is claimed is:

1. An orthodontic bracket comprising:
   a body configured to be adhered to a tooth;
   a cover coupled to the body such that the cover is capable of linear and rotational movement; and
   an elastic member configured to press the cover to maintain a locked state of the cover,
   wherein the body comprises a wire slot, an attachment surface configured to be adhered to the tooth, a guide part and a body locking part, the guide part having a guide recess formed with an inclination angle, the body locking part being configured to latch onto the cover,
   the cover comprises a hinge part and a cover locking part, the hinge part having a hinge protrusion configured to be inserted into the guide recess to enable linear and rotational movement, the cover locking part being configured to be latched onto the body locking part,
   an upper end of the guide recess is open to receive the hinge protrusion of the hinge part for installation and a lower end of the guide recess is completely closed to limit a downward linear movement of the hinge part of the cover such that the cover remains engaged from the guide recess even when the cover locking part is not properly latched onto the body locking part,
   a distance between the upper end and the body locking part is less than a distance between the lower end and the body locking part,
   a distance between the upper end and the attachment surface of the body is greater than a distance between the lower end and the attachment surface, and
   after the hinge part of the cover is installed in the guide recess, the hinge part of the cover linearly moves along the guide recess when the cover moves from an open position to a locked position.

2. The orthodontic bracket of claim 1, wherein the guide recess is formed in each of a left and a right side of the guide part, and the cover includes a pair of the hinge protrusions facing each other.

3. The orthodontic bracket of claim 1, wherein the guide recess is formed in a sloping fashion.

4. The orthodontic bracket of claim 1, wherein the body locking part comprises a locking protrusion and a cover holder recess, the cover holder recess is configured to receive a portion of the cover inserted therein, and the cover locking part is inserted into the cover holder recess and latched onto the locking protrusion.

5. The orthodontic bracket of claim 4, wherein the locking protrusion comprises a latching protrusion, and the cover locking part comprises a latching recess configured to receive the latching protrusion inserted therein.

6. The orthodontic bracket of claim 4, wherein the cover holder recess has an elastic member insertion recess formed therein, the elastic member insertion recess being configured to receive the elastic member inserted therein.

7. The orthodontic bracket of claim 1, wherein the body locking part comprises a locking protrusion slope, and the cover moves downward along the locking protrusion slope when the cover is coupled with the body.

8. The orthodontic bracket of claim 1, further comprising:
   an auxiliary elastic member configured to elastically press the cover,
   wherein the guide part has an auxiliary elastic member insertion recess formed therein, the auxiliary elastic member insertion recess being configured to receive the auxiliary elastic member inserted therein.

9. The orthodontic bracket of claim 1, wherein the cover comprises a cover top surface and a cover sloped surface, and when the cover is coupled to the body, the cover sloped surface contacts the body locking part to stop a progress of the cover.

10. The orthodontic bracket of claim 9, wherein any one of the cover top surface and the cover sloped surface has a cover recess formed therein in intaglio.

11. The orthodontic bracket of claim 1, wherein the guide part has a smaller width than the body and is arranged at a center of the body, and the cover has a same width as the body.

12. The orthodontic bracket of claim 1, wherein the hinge part covers the guide recess.

13. The orthodontic bracket of claim 1, wherein the cover locking part covers a side surface of the body locking part.

* * * * *